United States Patent [19]

Nobel

[11] Patent Number: 5,847,204

[45] Date of Patent: Dec. 8, 1998

[54] PROCESS FOR PRODUCING AN IRIDIUM SOLUTION AND USE OF SAME AS CATALYST

[75] Inventor: Dominique Nobel, Fontaines-Saint-Martin, France

[73] Assignee: Acetex Chimie, Paris La Defense 2, France

[21] Appl. No.: 663,096

[22] PCT Filed: Dec. 28, 1994

[86] PCT No.: PCT/FR94/01542

§ 371 Date: Sep. 27, 1996

§ 102(e) Date: Sep. 27, 1996

[87] PCT Pub. No.: WO95/17963

PCT Pub. Date: Jul. 6, 1995

[30] Foreign Application Priority Data

Dec. 29, 1993 [FR] France .................................... 93 15825

[51] Int. Cl.⁶ ............................. C07C 51/12; C07C 51/14
[52] U.S. Cl. ......................... 562/519; 562/517; 562/520; 562/522; 562/591; 502/151; 502/152; 502/161; 502/325
[58] Field of Search ..................... 562/519, 517, 562/520, 522, 591; 502/151, 152, 161, 325

[56] References Cited

U.S. PATENT DOCUMENTS

| 3,772,380 | 11/1973 | Paulik et al. | 560/232 |
| 3,818,060 | 6/1974 | Forster et al. | 554/129 |
| 4,060,547 | 11/1977 | Paulik et al. | 562/519 |
| 5,227,522 | 7/1993 | Denis et al. | 562/522 |
| 5,420,346 | 5/1995 | Denis et al. | 562/522 |

FOREIGN PATENT DOCUMENTS

| 0 045637 | 2/1982 | European Pat. Off. . |
| 0 511 126 | 10/1992 | European Pat. Off. . |
| 0 536 064 | 4/1993 | European Pat. Off. . |
| 93/12063 | 6/1993 | European Pat. Off. . |
| 2 280 622 | 2/1976 | France . |

*Primary Examiner*—Gary Geist
*Assistant Examiner*—Rosalynd Keys
*Attorney, Agent, or Firm*—Burns, Doane, Swecker & Mathis, L.L.P.

[57] ABSTRACT

An iridium-based solution is prepared by contacting components in a liquid phase containing (a) a carbonylated iridium compound, (b) hydriodic acid, a precursor of such an acid, or mixture thereof, and (c) a solvent; under a total pressure of between 1 and 10 bar at a temperature not greater than the boiling temperature of the solvent under conditions in which the components are brought into contact. The iridium-based solution can be used as a catalyst for carrying out carbonylation, hydroformylation or isomerization reactions.

11 Claims, No Drawings

PROCESS FOR PRODUCING AN IRIDIUM SOLUTION AND USE OF SAME AS CATALYST

This application is a national stage application under 35 U.S.C. §371 of PCT/FR94/01542, filed Dec. 28, 1994.

The present invention relates to the preparation of an iridium-based solution and to the use of the latter as catalyst.

Iridium is a well-known catalyst which is used in many types of reactions. Mention may be made, by way of example, of the use of iridium-based catalytic systems in carbonylation reactions of compounds of the alcohol, ether or carboxylic acid eater type with the aim of manufacturing in particular carboxylic acids or carboxylic acid anhydrides. Applications of iridium as catalyst in hydroformylation reactions of olefins to obtain aldehydes are also known. This catalyst can likewise be used to produce acetic acid by isomerization of methyl formate or alternatively in the water gas reaction.

In the more specific case of producing carboxylic acids by carbonylation, American Patent U.S. 3,772,380 describes the use of a catalytic system, which exists in a form which is soluble or insoluble in the reaction medium, based on iridium, one of the ligands of which is a halogen, and on a covalent halide (alkyl halide, for example). The iridium can be introduced into the reaction mixture either directly in the form of a compound comprising a halogen or in the form of two separate compounds constituting precursors of the final compound comprising the iridium and the halogen.

However, the existence is observed of many disadvantages in carrying out the process, as described in this patent, on an industrial scale, and more particularly in the context of a catalysis carried out in a homogeneous phase.

First of all, this patent describes the direct introduction into the reaction medium of a precursor of the catalyst in a solid form. This does not correspond to industrial practice and is the cause of implementational difficulties. The first relates to the fact that the conversion of the solid compound to a catalytically active compound is reflected by an initiation period during which the productivity is not optimum and the formation of by-products very often increased. The second is related to the fact that the conversion to an active compound which is soluble in the reaction medium cannot be monitored. For example, it is not obvious that the said conversion is complete and, if it is not complete, that this does not lead to a fall in activity and is not the cause of a loss of catalyst, by entrainment or other cause.

Moreover, compounds are found, among the precursors mentioned, which contain components foreign to the system which risk contaminating the reaction medium or alternatively disturbing the behaviour of the reaction.

It should also be noted that, in this patent, the conversion to an active compound is carried out under the conditions of the reaction for which the catalyst is subsequently used, that is to say under very severe conditions since the temperature and the pressure are high.

One of the aims of the present invention is therefore to propose an iridium-based solution which can be used directly as catalyst, which can be used on an industrial scale and which does not have the abovementioned disadvantages, whether as regards the preparation of the said solution or its use.

Thus, the present invention makes it possible to obtain an iridium-based solution by implementing a simple process under gentle conditions which do not require in particular use of high pressure and high temperature. For this reason, the necessary equipment in which the conversion takes place is conventional equipment and less expensive than equipment capable of resisting high pressures.

The invention likewise makes it possible to prepare an iridium-based solution which does not comprise components foreign to the subsequent reaction in which it will be employed.

Another aim of the invention is to obtain concentrated iridium solutions. This represents a particularly worthwhile advantage, from an industrial angle, since it makes it possible to reduce the size of the equipment used for preparing the solution or alternatively the number of production campaigns necessary to obtain the desired amount of soluble iridium compound.

Finally, a subject of the invention is the preparation of an iridium-based solution which is directly active when it is used as catalyst, that is to say without an initiation period.

These aims and others are obtained by the present invention which consists in bringing a carbonylated iridium compound into contact, in the liquid phase, with hydriodic acid or a precursor of such an acid, in the presence of a solvent, under a total pressure of between 1 and 10 bar and at a temperature not greater than the boiling temperature of the abovementioned solvent under the conditions under which the reactants are brought into contact.

A subject of the invention is likewise the use, as catalyst, of the iridium-based solution which is capable of being obtained by implementation of such a process.

However, other advantages and characteristics of the present invention will become more clearly apparent on reading the description and examples which will follow.

As has been indicated above, the process consists in using, as iridium-based compound, a complex comprising iridium and at least one ligand of carbonyl type. Mention may be made, by way of example, of $Ir_4(CO)_{12}$.

The iridium-based compound is therefore brought into contact with hydriodic acid, a precursor of this acid or their mixture.

Mention may be made, as precursor capable of releasing hydriodic acid, of, for example, iodine or $C_1$–$C_{10}$ alkyl iodides.

Hydriodic acid can be used in the form of a solution or alternatively in the gas form.

According to a preferred embodiment of the invention, hydriodic acid is used in the form of a solution and more particularly in the form of an aqueous solution. Although any degree of dilution of the acid is suitable for the implementation of the process, it is preferable to use aqueous solutions having an acid content of between 40 and 70%.

The amount of hydriodic acid involved in the process according to the invention varies within wide limits.

More particularly, the amount of hydriodic acid is such that the number of moles of acid, with respect to the number of moles of iridium, varies between 1 and 20.

These two compounds are brought into contact in the presence of a solvent.

Any compound can be used insofar as it dissolves hydriodic acid or its precursor and the iridium-based compound obtained. However, use is more particularly made of solvents chosen from water, saturated or unsaturated, linear, branched or cyclic carboxylic acids comprising from 1 to 10 carbon atoms, esters of saturated or unsaturated, linear, branched or cyclic carboxylic acids comprising 2 to 20 carbon atoms, or linear, branched or cyclic alkenes or alternatively alkynes comprising 2 to 20 carbon atoms, these compounds being taken alone or as a mixture.

The choice of solvent is preferably determined as a function of the subsequent application of the solution obtained. Thus, by way of example, it is possible to choose acetic acid and/or methyl acetate in the case of preparation of acetic acid. It is possible to use adipic acid, 3-pentenoic acid and/or corresponding esters, or alternatively butadiene, to produce adipic acid.

It has been found, in an entirely surprising and advantageous way, that the iridium-based compound, when brought into contact with hydriodic acid and/or a precursor, was converted into a soluble, catalytically active compound under very mild temperature and pressure conditions.

In fact, the process according to the invention is implemented under a total pressures of between 1 and 10 bar.

According to a preferred embodiment of the invention, the total pressure is from 1 to 5 bar. According to an even more preferred embodiment, the total pressure is between 1 and 3 bar.

Moreover, the reaction is carried out at a temperature not greater than the boiling temperature of the solvent under the pressure conditions mentioned above.

The atmosphere under which the process of the invention is implemented is immaterial and this represents not only a certain advantage with respect to how it was known to behave but also an entirely unexpected phenomenon.

In fact, it has been found that the conversion to a soluble iridium compound could be carried out under air. It was absolutely not obvious to those skilled in the art, on the one hand, that the said iridium compound is converted to a soluble compound under such conditions and, on the other hand, that the resulting compound is stable. It is restated here that known processes are exclusively implemented under a high carbon monoxide partial pressure and that such solutions are used immediately after their preparation, if not simultaneously.

The atmosphere in question can also be a carbon monoxide atmosphere but at pressures which are not comparable with those generally used.

It is likewise possible to carry out the process of the invention under a rare gas such as argon or helium, under nitrogen or alternatively under hydrogen.

It is specified that it in possible to envisage carrying out the reaction under conditions in which a mixture of the abovementioned gases is present.

The choice of the atmosphere under which the conversion takes place is advantageously a function of the subsequent use of the solution prepared. In fact, in the majority of the reactions mentioned for which the abovementioned solution can be used as catalyst, a controlled atmosphere is necessary. Thus, for carbonylation reactions, the gas is generally carbon monoxide. It is generally likewise the case for hydroformylation reactions.

Consequently, it can be advantageous to carry out the reaction according to the invention by right away using a gas desired for the subsequent reaction.

The present invention makes it possible to obtain concentrated soluble iridium solutions since they can contain up to 3% iridium. Moreover, it is important to note that such solutions are stable with time, even at such concentrations, without it being necessary to store them under a specific atmosphere, such as, for example, carbon monoxide or an inert gas such as nitrogen.

The operation proper of bringing the reactants into contact can be carried out according to any method known to those skilled in the art.

Thus, the iridium-based compound can be introduced into hydriodic acid or a precursor of this acid, it being known that it is possible to carry out a reverse introduction or to bring the two reactants into contact simultaneously.

Moreover, one and/or the other of these two compounds can be brought into contact directly or else each in the form of a mixture with one or more of the abovementioned solvents.

In the case where the process is carried out under a gas other than air, this can be installed before or during the operation of bringing the reactants into contact.

Another possibility which can be envisaged, which is suitable for immediate use of the iridium-based solution, is to carry out the operation of bringing the reactants into contact under air. Then, before introducing the solution obtained into the reaction medium, the air is purged in order to replace it by the atmosphere appropriate to the subsequent reaction in which the said solution is involved as catalyst.

The operation of bringing the reactants into contact is conventionally carried out with stirring.

It should be noted that the process according to the invention makes it possible to dissolve all the iridium present. However, there would not be any specific problem if all the iridium involved was not converted to a soluble compound. In fact, in most industrial processes, the main objective is not to obtain the highest possible yield but to find a compromise between productivity (profitability) and yield.

Thus, the duration of the operation is not critical and a person skilled in the art is able to set it according to whether he favours the profitability of the process or alternatively maximum solubilization of the iridium compound. By way of indication, this time varies between about 10 minutes and about 20 hours.

As has been mentioned previously, another subject of the invention relates to the use of the said iridium-based solution as catalyst.

The solution obtained by the process according to the invention can advantageously be used as is for the reaction, as is the case for homogeneous-phase catalyses.

It can likewise be used to prepare a solid catalyst (supported or unsupported) by applying conventional methods.

It is thus possible to envisage drying the solution obtained, optionally in the presence of a support suitable for the reaction in which the catalyst is intended to be used, so as to obtain iridium-based particles. Moreover, it is possible to impregnate the said support, each of the abovementioned stages (drying, impregnation) optionally being followed by periods of heating/sintering.

However, according to a preferred embodiment of the invention, the solution is used as catalyst, or part of a catalytic system, for carrying out homogeneous-phase reactions.

The solution obtained according to the invention can be brought directly into contact with the reaction mixture or else can be treated beforehand in order to make it entirely compatible with the said reaction medium. Prior treatment is understood, in particular, to mean adjusting the contents of some of the compounds of the solution or completing the composition of the solution by adding thereto constituents which were not found therein on conclusion of its process of preparation or else alternatively changing the atmosphere under which the solution is found.

The said solution can more particularly be used for carrying out carbonylation, hydroformylation or isomerization reactions.

According to a preferred embodiment, the present solution in employed in carrying out carbonylation reactions in the presence of carbon monoxide, in the liquid phase, with a view to obtaining carboxylic acids and/or carboxylic acid anhydrides. It should be noted that this type of reaction is well known and that it has formed the subject of many patents and publications. Consequently, the reaction conditions set out below are given only in a general capacity and cannot be regarded as limiting.

The reactants used for this type of reaction are chosen from saturated or unsaturated, linear, branched or cyclic hydrocarbon compounds. Mention may be made, by way of illustration, of $C_2$–$C_{10}$ alkenes or alkynes, $C_1$–$C_{10}$ alcohols, the halogenated derivatives of the said alcohols, $C_2$–$C_{20}$ ethers, $C_3$–$C_{10}$ carboxylic acids, comprising at least one unsaturation, $C_2$–$C_{20}$ carboxylic acid esters as well as the halogenated derivatives of the said esters.

The catalytic system conventionally comprises, on the one hand, the iridium-based solution and, on the other hand, a halogenated promoter preferably chosen from iodinated derivatives such as alkyl iodides.

The process generally consists in reacting one of the reactants mentioned above in the presence of the catalytic system and carbon monoxide at a temperature varying from 50° to 300° C. and at a total pressure of between 5 and 200 bar.

The reaction is generally carried out in the presence of a solvent which is more particularly chosen from the products and/or reactants used in the reaction.

Depending on whether the objective of the reaction is to obtain the carboxylic acid (or the corresponding ester) or the carboxylic acid anhydride, the reaction is carried out under anhydrous or non-anhydrous conditions. Thus, in the first case, the reaction medium generally comprises water whereas this cannot be the case during the production of anhydride.

A preferred application of the catalytic solution according to the invention consists in carrying out the carbonylation of alcohols, or of the corresponding halogenated derivatives, to carboxylic acids.

In the last case, the reaction in preferably carried out while maintaining, in the reaction medium, contents of water, of halogenated promoter and of alcohol of between 0 exclusive and 10% and a content of ester, corresponding to the alcohol and to the carboxylic acid formed, of between 2 and 40%, the remainder consisting of the said acid formed.

Concrete non-limiting examples of the invention will now be presented.

EXAMPLES

Example 1

This example illustrates the preparation according to the invention while using acetic acid as solvent.

The following are introduced into a glass round-bottomed flask:

10 g of $Ir_4(CO)_{12}$;

50 g of hydriodic acid as a 57% solution in water;

290 g of acetic acid.

The mixture obtained is heated with stirring and under air at reflux (=120° C.).

The duration of the reaction is 4 hours.

A homogeneous solution is obtained.

The iridium dissolved in the liquid phase is quantitatively determined by atomic absorption spectroscopy and it is observed that 100% of the iridium introduced is in solution.

The solution obtained was stored for several months under air without precipitation being observed.

Example 2

This example illustrates the preparation according to the invention while using 3-pentenoic acid as solvent.

The following are introduced into a glass round-bottomed flask:

0.5 g of $Ir_4(CO)_{12}$;

1 g of hydriodic acid as a 57% solution in water 38.8 g of 3-pentenoic acid.

The mixture obtained in heated with stirring and under air at reflux (=150° C.).

The duration of the reaction is 2.5 hours.

A homogeneous solution is obtained. The iridium dissolved in the liquid phase is quantitatively determined by atomic absorption spectroscopy and it is observed that 100% of the iridium introduced is in solution.

The solution obtained was stored for several months under air without precipitation of an iridium-based compound being observed.

Comparative Example 3

This example is carried out while not using hydriodic acid.

The following are introduced into a glass flask:

0.11 g of $Ir_4(CO)_{12}$;

7.2 g of methyl iodide;

20 g of methanol;

49.5 g of acetic acid.

The mixture obtained is heated with stirring and under air at reflux (=120° C.).

The duration of the reaction is 4 hours.

A suspension is obtained. The latter is filtered and the iridium dissolved in the liquid phase is quantitatively determined by atomic absorption spectroscopy. It in observed that 15% of the iridium involved is in solution.

Example 4

The subject of this example is the application of the catalytic solution obtained in Example 1 for the carbonylation of methanol to acetic acid.

The following are introduced into a Hastelloy® B2 autoclave (Haynes):

2.9 g of the solution obtained in Example 1;

2.16 g of water;

0.5 g of methanol;

8.6 g of methyl acetate;

2.5 g of methyl iodide;

54.6 g of acetic acid.

The autoclave is pressurized with 5 bar of carbon monoxide.

The temperature is brought to 190° C. and then, once the required temperature has been reached, a total pressure of 30 bar is established by means of carbon monoxide.

Under these conditions, the rate of carbonylation of the methanol, obtained by measuring the rate of consumption of the carbon monoxide, is 4.2 mol/h.l. The existence of an initiation period of the reaction was not observed (the rate mentioned above was immediately achieved).

Example 5

The subject of this example the application of the catalytic solution obtained in Example 2 for the carbonylation of 3-pentenoic acid to adipic acid.

The following are introduced into a glass flask:

0.85 g of the solution obtained in Example 2;

0.87 g of water;

9.4 g of 3-pentenoic acid.

The flask is placed in a Hastelloy® B2 autoclave (Haynes) which is pressurized with 5 bar of carbon monoxide.

The temperature is brought to 185° C. and then, once the required temperature has been reached, a total pressure of 20 bar is established by means of carbon monoxide.

Under these conditions, the rate of carbonylation of the 3-pentenoic acid, obtained by measuring the rate of consumption of the carbon monoxide, is 8 mol/h.l. The existence of an initiation period of the reaction was not observed (the rate mentioned above was immediately achieved).

Comparative Example 6

This example illustrates the preparation and simultaneously the use of the catalyst obtained in a carbonylation reaction of 3-pentenoic acid.

The following are introduced into a glass flask:

10.8 mg of $Ir_4(CO)_{12}$;

21.4 mg of hydriodic acid as a 57% solution in water;

0.8 g of water;

10.1 g of 3-pentenoic acid.

The flask is placed in a Hastelloy® B2 autoclave (Haynes) which is pressurized with 5 bar of carbon monoxide.

The temperature is brought to 185° C. and then, once the required temperature has been reached, a total pressure of 20 bar is established by means of carbon monoxide.

Under these conditions, an initiation period of 30 minutes is observed and then the rate of carbonylation is measured, by measuring the rate of consumption of the carbon monoxide. The latter is 4.4 mol/h.l.

We claim:

1. A process for the preparation of an iridium-based solution, said process comprising contacting in a liquid phase:

(a) a carbonylated iridium compound;

(b) hydriodic acid, a precursor of such an acid, or mixture thereof; and (c) a solvent; under a total pressure of between 1 and 10 bar at a temperature not greater than the boiling temperature of the solvent under conditions in which the components are brought into contact, wherein the number of moles of hydriodic acid, with respect to the number of moles of iridium, is between 1 and 20, and the contacting is carried out under an atmosphere selected from the group consisting of air, rare gases, nitrogen, hydrogen and mixtures thereof.

2. The process according to claim 1, wherein the reactants are brought into contact under a total pressure of between 1 and 5 bar.

3. A process according to claim 1, wherein said solvent is selected from the group consisting of water, saturated or unsaturated, linear, cyclic or branched carboxylic acids comprising 1 to 10 carbon atoms, esters of saturated or unsaturated, linear, cyclic or branched carboxylic acids comprising 2 to 20 carbon atoms, linear, cyclic or branched alkenes or alkynes comprising 2 to 20 carbon atoms, or mixtures thereof.

4. A process according to claim 1, wherein the reactants are brought into contact under a rare gas, nitrogen, hydrogen, or mixture thereof.

5. The process according to claim 2, wherein the pressure is between 1 and 3 bar.

6. The process according to claim 4, wherein the rare gas is argon or helium.

7. A catalyst prepared by the process of claim 1.

8. A process for conducting carbonylation, hydroformylation or isomerization, said process comprising exposing a compound capable of being carbonylated, hydroformylated or isomerized, to the iridium-based solution prepared according to the process of claim 1.

9. A process for carbonylating a compound, said process comprising exposing a compound selected from the group consisting of linear, cyclic or branched $C_2$–$C_{10}$ alkenes or alkynes, saturated or unsaturated, linear, cyclic or branched $C_1$–$C_{10}$ alcohols; halogenated derivatives of said alcohols; saturated or unsaturated, linear, cyclic or branched $C_2$–$C_{20}$ ethers; linear, cyclic or branched $C_3$–$C_{10}$ carboxylic acids comprising at least one unsaturation; saturated or unsaturated, linear, cyclic or branched $C_2$–$C_{20}$ carboxylic acid esters and halogenated derivatives of said esters, to the iridium-based solution prepared according to the process of claim 1.

10. The process according to claim 1, wherein said carbonylated iridium compound is $Ir_4(CO)_{12}$.

11. The process according to claim 1, wherein said atmosphere is air.

* * * * *